(12) United States Patent
Gupta et al.

(10) Patent No.: US 7,138,528 B2
(45) Date of Patent: Nov. 21, 2006

(54) METHOD FOR CRYSTALLIZING N-VINYL-2-PYRROLIDONE

(75) Inventors: Vijai P. Gupta, Berwyn, PA (US); Edward P. Carey, Atglen, PA (US)

(73) Assignee: Lyondell Chemical Technology, L.P., Houston ( * ) Notice: Subject to any disclaimer, the term of this patent is extended or adjusted under 35 U.S.C. 154(b) by 101 days.

(21) Appl. No.: 11/047,843

(22) Filed: Feb. 1, 2005

(65) Prior Publication Data

US 2006/0173194 A1    Aug. 3, 2006

(51) Int. Cl.
*C07C 207/267*    (2006.01)

(52) U.S. Cl. .................................................. 548/555

(58) Field of Classification Search ................ 548/555
See application file for complete search history.

(56) References Cited

U.S. PATENT DOCUMENTS

| | | | |
|---|---|---|---|
| 4,801,760 A | 1/1989 | Gupta | 568/923 |
| 5,039,817 A | 8/1991 | Kroker et al. | 548/543 |
| 5,329,021 A | 7/1994 | Cohen et al. | 548/543 |
| 5,710,284 A * | 1/1998 | Schmidt-Radde et al. | 548/543 |
| 5,755,975 A | 5/1998 | Eck et al. | 210/714 |
| 6,436,243 B1 | 8/2002 | Yamaguchi et al. | 203/2 |
| 6,703,511 B1 | 3/2004 | Eck et al. | 548/543 |

* cited by examiner

*Primary Examiner*—Kamal A. Saeed
*Assistant Examiner*—Joseph R. Kosack
(74) *Attorney, Agent, or Firm*—Jonathan L. Schuchardt

(57) ABSTRACT

A method for purifying N-vinyl-2-pyrrolidone (NVP) is disclosed. The method comprises crystallizing NVP in the presence of added water to produce purified NVP crystals and a mother liquor, and then isolating the purified crystals. In a preferred method, 0.5 to 4 wt. % of water based on the amount of NVP to be purified is added, and the NVP crystals are washed with additional pure NVP, preferably NVP crystal melt, to give crystals having a purity greater than 99.99%. The method provides a fast, effective way to generate and isolate pure NVP in a single-stage crystallization.

11 Claims, No Drawings

METHOD FOR CRYSTALLIZING N-VINYL-2-PYRROLIDONE

FIELD OF THE INVENTION

The invention relates to a method for purifying N-vinyl-2-pyrrolidone by crystallization.

BACKGROUND OF THE INVENTION

N-Vinyl-2-pyrrolidone (NVP) is a monomer used for making crosslinked or uncrosslinked polyvinylpyrrolidones, vinyl pyrrolidone-vinyl ester copolymers, and other valuable polymers. The polymers are used in beverage clarification, hair care, pharmaceutical tablet binding, and other industrial applications.

NVP is commonly purified by fractional distillation to remove unreacted starting materials and side-products. For a recent example, see U.S. Pat. No. 6,436,243. It can also be purified by treatment with an acidic ion-exchange resin (see U.S. Pat. No. 5,039,817). Fractional distillation provides "industrial grade" NVP that is 98–99.5% pure, but this purity level can be inadequate for beverage clarification, cosmetics, and pharmaceutical uses. In particular, industrial grade NVP often contains traces of close-boiling impurities such as 2-pyrrolidone (2-Py), N-ethylpyrrolidone (NEP), and gamma-butyrolactone (GBL).

Multi-stage, melt crystallization is used to upgrade industrial grade NVP to "pharmaceutical grade" NVP, which is more than 99.9% pure, and often more than 99.99% pure. The process is costly, requires expensive equipment, and is time-consuming. In a melt crystallization process, NVP is cooled below 14° C. (its nominal freezing point) to promote crystallization. As crystals form, they are separated from the mother liquor. The process is repeated to achieve a desired purity level. Unfortunately, because the NVP is usually quite pure already, the temperature must be controlled with great care to prevent the entire mass from rapidly solidifying or to prevent already-crystallized NVP from melting back into the mother liquor. Separating and handling crystals that are at a temperature only slightly below their melting point is difficult, as the crystals tend to melt quickly with even a slight temperature increase or disturbance.

U.S. Pat. No. 5,329,021 describes a melt crystallization process in which NVP is cooled 1° C. to 5° C. below its freezing point to induce crystal formation, the crystals are separated from the remaining mother liquor and are liquified, and the purified liquid is subjected to one or more additional crystallization stages. This process suffers from the need for careful temperature control, rapid freezing of supercooled liquid to a solid mass, and rapid melting of isolated crystals. Thus, there is a premium on the ability to control temperature accurately and precisely. The tight temperature window makes it difficult to separate the crystals from the mother liquor, thus reducing the efficacy of the crystallization step.

In another approach, crystallizer surfaces are covered with a seed layer of crystallized NVP to induce crystallization of the impure NVP liquid (see U.S. Pat. Nos. 5,710,284 and 5,755,975). This method reduces the reliance on supercooling but otherwise suffers from most of the drawbacks noted above.

U.S. Pat. No. 6,703,511 teaches to improve the crystallization process by adding a side-purification routine. Mother liquor from the first crystallization stage is distilled or is subjected to an extractive workup to remove impurities. The purified mother liquor is then returned to the crystallizer. An ideal crystallization method for NVP would sidestep supplemental purification schemes.

The industry would benefit from better ways to purify NVP. In particular, an improved way of crystallizing industrial grade NVP to produce pharmaceutical grade NVP is needed. Preferably, the method would overcome the need for expensive equipment, precise temperature control, multiple crystallizations, or seeding techniques. An ideal method would provide NVP crystals that can be easily isolated from the mother liquor and can be handled or transferred without rapid remelting.

Recently, we found that adding water to NVP depresses both the melting and freezing points of the NVP/water mixture, but it does so differentially. This interesting observation prompted us to devise conditions under which NVP can be effectively and efficiently purified by crystallization.

SUMMARY OF THE INVENTION

The invention is method for purifying N-vinyl-2-pyrrolidone (NVP). The method comprises: (a) crystallizing NVP in the presence of added water to produce purified NVP crystals and a mother liquor; and (b) separating the NVP crystals from the mother liquor. In a preferred method, the crystallization is performed in the presence of 0.5 to 4 wt. %, based on the amount of NVP to be purified, of added water.

Adding a small proportion of water to NVP strongly depresses the freezing point of the mixture such that the mixture can be cooled substantially below the normal freezing point of NVP. This enables formation of a thick, free-flowing slush containing NVP crystals and mother liquor. Because the NVP crystals in the slush are considerably below their melting point (i.e., "sub-cooled"), they are easy to isolate. The wide temperature window between initial crystal formation and thick slush formation eliminates the need for precise temperature control. This simple method can provide NVP with a purity greater than 99.99%.

DETAILED DESCRIPTION OF THE INVENTION

N-Vinyl-2-pyrrolidone (NVP) is commercially available from BASF Corporation. It can also be made by well-known processes, including vinylation of 2-pyrrolidone or dehydration of N-(2-hydroxyethyl)-2-pyrrolidone. The source of the NVP is not critical. The method of the invention will benefit most commercial and non-commercial sources of NVP. The method is particularly well-suited for converting industrial grade NVP, which has a purity less than about 99.5%, to pharmaceutical grade NVP, which has a purity greater than 99.9%.

The method of the invention comprises two steps. NVP is first crystallized in the presence of added water. The resulting crystals are then separated from the mother liquor.

By "freezing point," we mean the temperature at which a chilled NVP/water slush within a test tube or other container solidifies enough that it can no longer be easily stirred by hand using a wisk. By "slush point," we mean the temperature at which the contents of the chilled container thicken with NVP crystals, but the mixture remains easy to stir with a wisk. By "melting point," we mean the temperature at which a warmed slush of NVP crystals and added water becomes completely liquified.

The crystallization can be performed using conventional equipment and common techniques. Unlike conventional melt crystallizations, the method of the invention does not require expensive equipment capable of precise temperature control. Example 2 (below), for instance, was performed using little more than a simple jacketed kettle, a chiller to circulate cooling fluid through the kettle, a mechanical stirrer, and a Buchner funnel to collect and wash crystals. The NVP-water mixture can simply be cooled until crystallization commences. Any suitable means can be used to remove the resulting NVP "slush" from the chilled surface to expose as much of the liquid mixture as possible to the chilled surfaces. For example, a scraped-surface heat exchanger can be used. Crystal formation occurs rapidly in the presence of the added water, but the mixture remains stirrable.

The method requires adding water to the NVP to be crystallized. The amount of water used is preferably an amount effective to achieve a significant differential between the melting and freezing points (as defined above) of the NVP/water mixture. In particular, it is preferred that the difference in the melting and freezing points be at least 3° C., preferably at least 4° C. Preferably, water is added in an amount within the range of 0.3 to 10 wt. %, more preferably from 0.5 to 4 wt. %, and most preferably from 1 to 2 wt. % based on the amount of NVP to be purified.

The crystallizations are typically performed within a temperature range that is below the normal freezing point of NVP. In particular, the crystallizations are preferably performed at a temperature within the range of −5° C. to 15° C., more preferably from 0° C. to 12° C., and most preferably from 4° C. to 10° C.

Pure NVP (no water added) has a melting point of 14.4° C. and a freezing point of 13.9° C. (see Table 1, below). Because of this 0.5° C. difference, NVP is difficult to purify simply by melt crystallization, especially when the purity level is already high. Any addition of energy used to separate crystals from mother liquor, e.g., by centrifugation, melts the crystals. When no water is added, the narrow temperature difference allows NVP to freeze solid to chilled surfaces of the crystallizer, thereby trapping mother liquor and its impurities within the solids (see Comparative Example 3, below). The frozen NVP adheres strongly to the chilled surface and usually is removed only by melting it off. The resulting liquid is compositionally almost identical to the liquid mixture from which it came, and little if any purification is achieved.

Adding water depresses the freezing point of an NVP/water mixture and expands the difference between the mixture melting and freezing points by 3° C. to 5° C. (see Table 1). Interestingly, the added water does not co-crystallize significantly in the NVP crystals. This allows the NVP/water mixture to be cooled well below the normal freezing point of NVP and enables formation of a thick, free-flowing slush that contains sub-cooled NVP crystals and water-enriched mother liquor. The method eliminates the need for precise temperature control because the NVP crystals can be easily isolated and handled without melting them.

Moreover, because the NVP crystals that develop are large and well defined, the mother liquor easily drains through them and the crystals can be easily washed with NVP crystal melt or other pure NVP. Additionally, the slush is easy to scrape from the chilled surfaces of the crystallizer, which allows more NVP to come into contact with those surfaces and crystallize. The slush remains stirrable even after it becomes thick with a high concentration of NVP crystals.

Any suitable means can be used to separate the NVP crystals from the mother liquor. Vacuum filtration is convenient. The crystals are preferably washed with additional pure NVP, preferably by allowing a small proportion of the crystals to melt in the filter funnel and pulling vacuum to draw the purified, melted liquid (i.e., "crystal melt") over the remaining crystals (see Example 2, which uses both techniques). Centrifugation can also be used either alone or in combination with a filtration technique. Centrifugation is helpful for removing water from the crystals. As shown in Table 2, significant levels of water can remain in the crystals if vacuum filtration alone is used. These values can be reduced significantly by combining the vacuum filtration with a centrifugation technique. Most of the water and other impurities can be removed, e.g., using a "pusher centrifuge" such as those manufactured by Kraus-Maffei or Baker Perkins. Because NVP is normally polymerized in aqueous media, however, the presence of some water in the crystals is usually innocuous.

Multiple crystallization stages can be used if desired to raise the purity of the NVP. At each stage, temperature changes only increase or decrease the thickness of the slush, so tight temperature control is not necessary. The concentration of water in the mother liquor increases with each crystallization. Each set of crystals is easy to recover by filtration and transfer for further handling. As Example 2 demonstrates, however, even a single-stage crystallization combined with crystal melt washing affords highly pure crystals.

As noted earlier, the method of the invention can be used to purify NVP having a variety of purity levels. It is particularly well suited, however, for purifying NVP that is already at least 98% pure (i.e., industrial grade NVP). The method is valuable for upgrading NVP from industrial to pharmaceutical grade, which generally needs to be at least 99.9% pure. We found that a single-stage crystallization in the presence of added water can provide NVP with a purity greater than 99.9%, preferably greater 99.99%, and more preferably greater than 99.999% (see especially Table 2, cuts 4 and 5).

The purity of each cut is determined by any suitable method, including gas chromatography, liquid chromatography, or the like. Gas chromatography is particularly convenient. Water content is conveniently monitored by Karl Fischer titration.

The method of the invention is simple, inexpensive, and easy to practice. It avoids the costly equipment, need for tight temperature control, use of seeding techniques, and side purification schemes taught by others. In sum, the invention provides a cost-effective way to generate and isolate NVP crystals having a purity greater than 99.99 wt. %.

The following examples merely illustrate the invention. Those skilled in the art will recognize many variations that are within the spirit of the invention and scope of the claims.

EXAMPLE 1

Freezing Point Depression of NVP with Water

N-Vinyl-2-pyrrolidone (NVP) is blended in test tubes with varying amounts of deionized water (1.4, 2.0, 4.0, 6.0, 8.0, and 10.0 wt. % based on the amount of NVP). Each blend is gently cooled while agitating with a hand wisk.

Temperatures are recorded for freezing point (wisk cannot be moved easily), slush point (tube is filled with solids, but wisk can be moved easily), and melting point (no crystals remaining). With no water added, these temperatures are almost superimposable; only about a 0.5° C. temperature difference is observed between melting and freezing points. When water is added, however, the freezing point of the NVP/water mixture is suppressed 4° C. to 5° C. more than the melting point (see Table 1). This substantial separation between freezing and melting points enables easier and more efficient melt crystallization of NVP.

TABLE 1

Freezing Point Depression of NVP with Added Water

| Wt. % Water in NVP/Water blend | Freezing point (° C.) | Slush point (° C.) | Melting point (° C.) |
| --- | --- | --- | --- |
| 0 | 13.9 | 13.7 | 14.4 |
| 1.4 | 7.8 | 9.5 | 11.6 |
| 2.0 | 7.0 | 8.4 | 10.4 |
| 4.0 | 3.5 | 4.7 | 7.5 |
| 6.0 | 1.1 | 1.3 | 4.9 |
| 8.0 | −0.7 | −2.1 | 2.7 |
| 10.0 | −3.1 | −3.5 | 1.1 |

EXAMPLE 2

Single-Stage Crystallization of NVP with Added Water

A 2-L jacketed kettle containing industrial grade NVP (1000 mL, see Table 2, "feed," for initial composition) and 2.0 wt. % of added deionized water is cooled with gentle stirring until the slush point is reached (about 6° C. to 7° C.). The solids temperature rises to about 9° C. from heat of fusion. Cooling continues. As crystals form on the surface of the kettle, they are scraped back into the slush. When crystallization is reasonably complete, the entire mass of NVP slush is transferred to a large Buchner funnel. The mother liquor drains through paper by gravity; a slight vacuum is applied to draw the remaining liquid through (total: about 250 mL of mother liquor containing about 5 wt. % water). The crystals are identified as "Cut 1."

The crystals are allowed to melt until another 50 mL of NVP drains by gravity. Again, a slight vacuum is applied to remove remaining liquid. The resulting crystals are labeled "Cut 2" (by GC analysis, 99.65% NVP).

The crystals are washed with 40 mL of warm (40° C.) previously crystallized NVP (99.99 wt. %). Vacuum assist recovers the wash NVP plus 20 mL of waste NVP from the crystals. The washed crystals are labeled "Cut 3" (99.994% NVP).

The washing step is repeated with another 40 mL of warm, previously crystallized NVP. The washed crystals are labeled "Cut 4" (99.999% NVP).

The crystals are allowed to melt at room temperature until 50 to 75 mL of liquid drains by gravity plus a vacuum assist. The crystals remaining are designated "Cut 5" (99.9997% NVP). Yield: 585 mL.

The mother liquors can be combined, if desired, and the method can be repeated to provide additional crops of purified NVP.

Table 2 summarizes the results and indicates the measured amount of water and volatile organics (by gas chromatography), including gamma-butyrolactone (GBL), N-methyl-2-pyrrolidone (NMP), N-ethyl-2-pyrrolidone (NEP), and 2-pyrrolidone (2-Py) in the purified NVP cuts.

TABLE 2

Crystallization of NVP with Added Water

| NVP Cut # | H$_2$O (wt. %) | Wt. % (by GC) | | | | |
| --- | --- | --- | --- | --- | --- | --- |
| | | NVP | GBL | NMP | NEP | 2-Py |
| Feed | 0.046 | 99.9164 | 0.0539 | 0.0034 | 0.0132 | 0.0131 |
| 1 | 2.86 | 99.8802 | 0.0688 | 0.0043 | 0.0271 | 0.0187 |
| 2 | 1.52 | 99.9645 | 0.0207 | 0.0037 | 0.0051 | 0.0060 |
| 3 | 0.82 | 99.9939 | 0.0034 | 0.0003 | 0.0009 | 0.0015 |
| 4 | 0.67 | 99.9992 | 0.0003 | ND | ND | 0.0005 |
| 5 | 0.29 | 99.9997 | 0.0001 | ND | ND | 0.0002 |

ND = none detected; GC = gas chromatography. GC results exclude the amount of water present, which is determined by Karl Fischer titration. NVP = N-vinyl-2-pyrrolidone; GBL = gamma-butyrolactone; NMP = N-methyl-2-pyrrolidone; NEP = N-ethyl-2-pyrrolidone; 2-Py = 2-pyrrolidone.

As the results demonstrate, industrial grade NVP can be converted to pharmaceutical grade NVP by a single-stage crystallization in the presence of added water. Multiple washings resulted in a more pure NVP product, with cut 3 at greater than 99.99% NVP, and cuts 4 & 5 at >99.999% NVP. The fifth cut product contained only 1 ppm of GBL, 2 ppm of 2-Py, and no detectable amount of NMP or NEP. The slush was easy to filter, and melting of the crystals was easy to control.

Significant (0.3 to 1.5 wt. %) water remains in the crystallized products (see Table 2). These values can be reduced by combining the vacuum filtration with a centrifugation technique as described earlier.

COMPARATIVE EXAMPLE 3

Melt Crystallization of NVP Without Added Water

The procedure of Example 2 is attempted without adding any water to the industrial grade NVP. Upon cooling, no slush results. The narrow temperature difference between melting and freezing points prevents formation of a manageable slush. Some of the NVP freezes solid to the kettle walls and cannot be removed by gentle scraping. The frozen material cannot be easily handled as a solid because it melts too quickly upon warming. GC analysis shows that the frozen solids are not significantly purer than the mother liquor from which they were removed.

The preceding examples are meant only as illustrations. The following claims define the invention.

We claim:

1. A method which comprises: (a) crystallizing liquid N-vinyl-2-pyrrolidone (NVP) in the presence of added water to produce purified NVP crystals and a mother liquor; and (b) separating the purified NVP crystals from the mother liquor.

2. The method of claim 1 wherein the water is added in an amount within the range of 0.5 to 4 weight percent based on the amount of NVP to be purified.

3. The method of claim 1 wherein the water is added in an amount within the range of 1 to 2 weight percent based on the amount of NVP to be purified.

4. The method of claim 1 wherein the crystallization is performed at a temperature within the range of −5° C. to 15° C.

5. The method of claim 1 wherein the crystallization is performed at a temperature within the range of 4° C. to 10° C.

6. The method of claim 1 wherein the purified NVP crystals are washed with additional pure NVP to a purity greater than 99.99%.

7. The method of claim 6 wherein the washing is repeated to provide NVP having a purity greater than 99.999%.

8. The method of claim 1 wherein separation step (b) is performed by filtration, centrifugation, or both.

9. A method which comprises: (a) crystallizing liquid N-vinyl-2-pyrrolidone (NVP) in the presence of 0.5 to 4 wt. % of added water at a temperature within the range of −5° C. to 15° C. to produce purified NVP crystals and a mother liquor; (b) separating the purified NVP crystals from the mother liquor; and (c) washing the purified NVP crystals with additional pure NVP to a purity greater than 99.99%.

10. The method of claim 9 wherein separation step (b) is performed by filtration, centrifugation, or both.

11. The method of claim 9 wherein step (c) is repeated to provide NVP having a purity greater than 99.999%.

* * * * *